United States Patent [19]

Wilson

[11] Patent Number: 4,646,682

[45] Date of Patent: Mar. 3, 1987

[54] WORM CONTAINER

[76] Inventor: Henry A. Wilson, 7461 W. Belvedera Blvd., West Palm Bch., Fla. 33411

[21] Appl. No.: 792,178

[22] Filed: Oct. 28, 1985

Related U.S. Application Data

[63] Continuation of Ser. No. 612,121, May 21, 1984, abandoned.

[51] Int. Cl.$^4$ ............................................... A01K 67/00
[52] U.S. Cl. .......................................... 119/1; 119/15
[58] Field of Search ....................................... 119/15, 1

[56] References Cited

U.S. PATENT DOCUMENTS

| | | | |
|---|---|---|---|
| 242,594 | 6/1881 | Brown | 220/228 |
| 1,018,277 | 2/1912 | Suhre | 43/121 |
| 1,568,625 | 1/1926 | Robinson | 220/354 |
| 2,642,836 | 6/1953 | Brooks | 119/15 |
| 3,468,289 | 9/1969 | Broida | 119/15 |
| 3,566,836 | 3/1971 | Elfert | 119/1 |
| 3,961,603 | 6/1976 | Gaddie, Sr. | 119/15 |

Primary Examiner—Hugh R. Chamblee
Attorney, Agent, or Firm—Eugene F. Malin

[57] ABSTRACT

A worm container cover including a planar cover extending inward from the sides with a central aperture. The aperture includes aperture sides projecting downwardly from said planar cover to provide access to a worm container covered by the container cover. The central aperture and aperture sides prevent easy escape of worm from the worm container. The planar cover includes a channel encircling the aperture. The channel may be filled with a liquid to prevent worms from being invaded by ants and the like.

6 Claims, 6 Drawing Figures

WORM CONTAINER

This application is a continuation of application Ser. No. 612,121, filed 5-21-84, now abandoned.

BACKGROUND OF THE INVENTION

This invention is to a worm container that has an aperture with downwardly projecting sides and a water filled channel surrounding the aperture.

It has been recognized that it is important to keep the enemies of worms out of the container as well as containing the worms therein. When a quantity of worm boxes are waiting buyers at one particular location a shallow pool may be built that will hold a great many containers in a pond of protective water. The water will protect the worms in the boxes from ants and the like. In the past pools or ponds have been built to hold a shallow pool of water to protect the worms in the containers.

The present invention gives protection to each worm container by using a depression in the container body or cover that may be filled with water so that the container is a self-contained barrier against ants. The container has sides and a bottom without openings and a top with an aperture and a trough or channel or depression encircling the aperture. The channel will contain a liquid to prevent any enemies of worms from entering the container. A screen may also be placed across the aperture to keep out larger enemies such as rodents.

BRIEF DESCRIPTION OF THE INVENTION

The present invention is to a worm container and container body and cover with an escape preventing system. The container cover includes a planar cover extending inward from the sides of the cover with a central aperture. The aperture includes aperture sides projecting downwardly from said planar cover to provide access to the container body of the worm container that is closed by the cover. The central aperture and aperture sides prevent easy escape of worm from the worms in the soil of the container.

The worm container is a worm box that will confine the worms in the enclosed area without the need of constant light. The container is designed so the worms will return back to the container each time he attempts to leave through the top of the container. The container is built in any form that will include an automatic system of returning the worm to the container. The worm may craw up in the material in the container and when the worm reaches the top surface of the material it will crawl along the bottom side of the planar cover until it encounters the aperture sides projecting downwardly into the container. These sides will force the worm to move downward into the container. It does not matter if this container is square, round or rectangular, or triangular or any other form as long as it includes the aperture side about the aperture. Any material may be used in constructing this container that will be able to contain a worm. The size of the container is a matter of choice.

The container also provides a protection system in the container body or cover. A liquid holding channel encircling the aperture. The channel is fillable with a liquid such as water to prevent enemies of worms from getting in the container. The worm container is a worm box that will prevent ants etc. from entering the container. The container is designed so that a water channel encircles the aperture in the container. The container is built in any form that will include a prevention system for keeping ants and the like out of the container. The ants may crawl up in the outside of the container but once met by the water filled channel it cannot reach the worms in the container.

It is an object of this invention to have a living area where the worms may live and multiply and not readily crawl away.

Another object of this invention is to provide a water barrier to protect the worms in the container from enemies.

A further object is to provide a container that may be separated to place it around a plant or that may be separated to remove it from around a plant.

In accordance with these and other objects which will be apparent hereinafter, the instant invention will now be described with particular reference to the accompanying drawings.

DESCRIPTION OF THE PREFERRED EMBODIMENT

Figure 1:
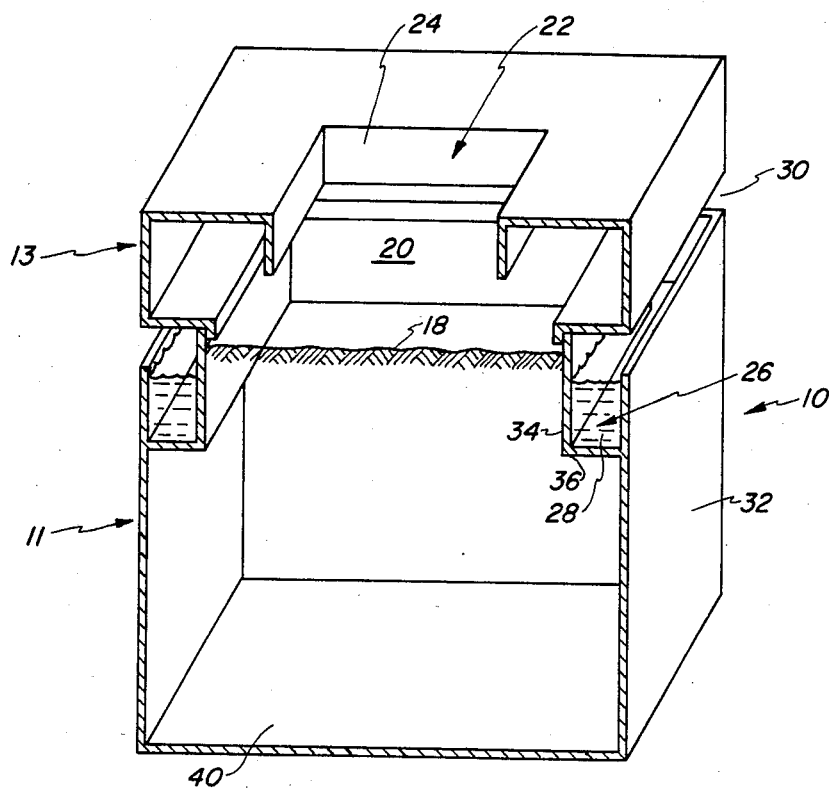
FIG. 1 illustrates an isometric cross section a container with an ant barrier in the form of a channel filled with water that the ants cannot cross and an aperture in the cover with encircling channel.

The worm container cover 13 in FIG. 1 prevents worms from escaping from the container. The container cover 13 includes a planar cover extending inward from the sides with a central aperture 22. The aperture 22 includes aperture sides 24 all around the aperture. The aperture sides 24 project downwardly from said planar cover to provide access to the worms in the container that are covered by the container cover 13. The central aperture 22 and aperture sides 24 prevent easy escape of the worm from the worm container. The worm container is a worm box that will confine the worms in the enclosed area below the dirt surface 18 without the need of constant light. The container is designated so the worms will return back into the container each time a worm moves upward and along the surface 18 as it attempts to leave through aperture 22. The container is built in any form that will include an automatic system of returning the worm to the container body 11. The worm may crawl up in the material in the container and when the worm reaches the top 18 it will crawl along the bottom side of the planar cover but it will be forced to move back into the container by the aperture sides.

In the container in FIG. 1 the channel 26 is filled with water 28 is in the sides 32 of the container body 11. The liquid holding channel 26 encircling the aperture 22. The channel is fillable with a liquid 28 such as water to prevent ants etc. from entering the worm container. The opening 30 prevents ants etc. from gaining access to aperture 22 without first crossing water 28 that lies in depression formed by sides 34 and 36.

Figure 2:
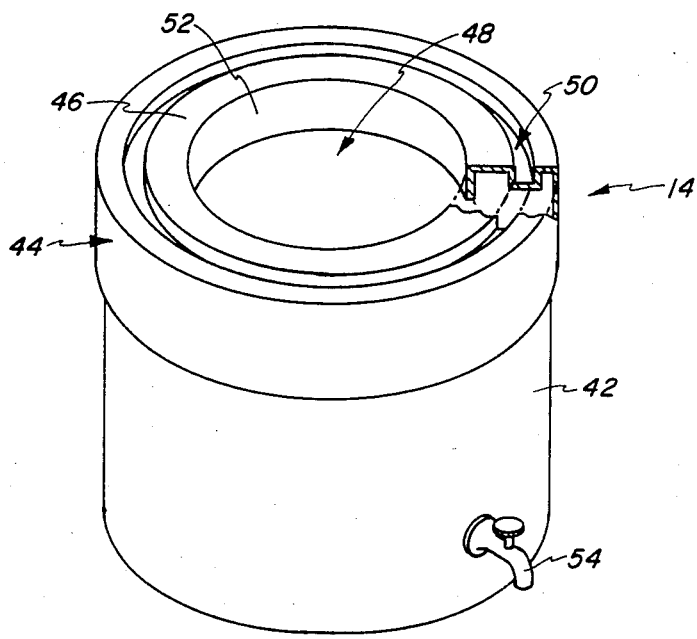
FIG. 2 is an isometric illustration of a round container and cover having an aperture and moat.

Referring now to FIG. 2 showing a round container 14 with a worm container cover 44 and worm container body 42 with the same escape preventing system as in FIG. 1. The container cover includes a planar cover 46 extending inward from the sides with a central aperture 48. The aperture includes an aperture side 52 projecting downwardly from said planar cover to provide access to a worm container body covered by the container cover 44. The central aperture and aperture sides prevent easy escape of worms from the worm containers. The container cover is also provided by a protective system. The planar cover includes a liquid holding channel 50 encircling the aperture 48. The channel is fillable with a liquid such as water to prevent ants etc. from entering the container. The container may include a sprocket to control the level of the liquid in the container 14.

Figure 3:
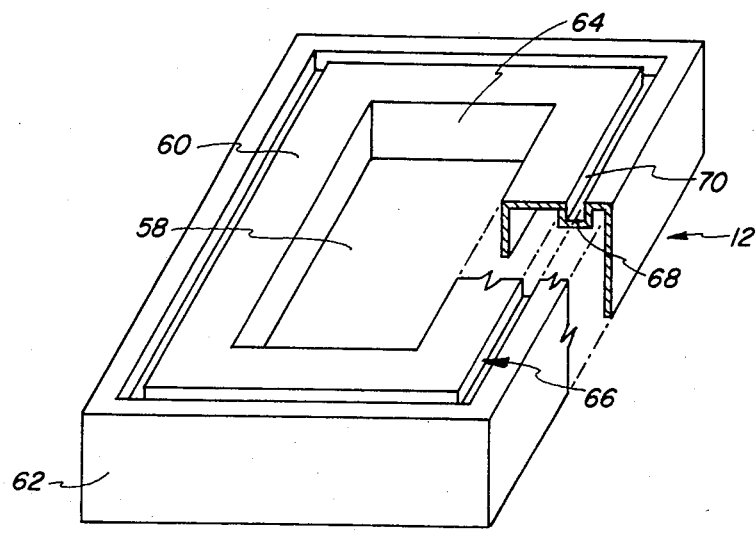
FIG. 3 is an isometric illustration of the cover of a container.

Referring now to FIG. 3 showing a worm container cover 12 with protective system 66 and escape preventing system 58 and 64. The container cover 12 includes a planar surface 66 extending inward from the sides 62 with a central aperture 58. The aperture 58 includes aperture sides 64 projecting downwardly from said planar cover. The planar cover also includes a liquid holding channel 66 encircling the aperture. The channel has sides 70 and bottom 68 that are fillable with a liquid such as water.

Figure 4:
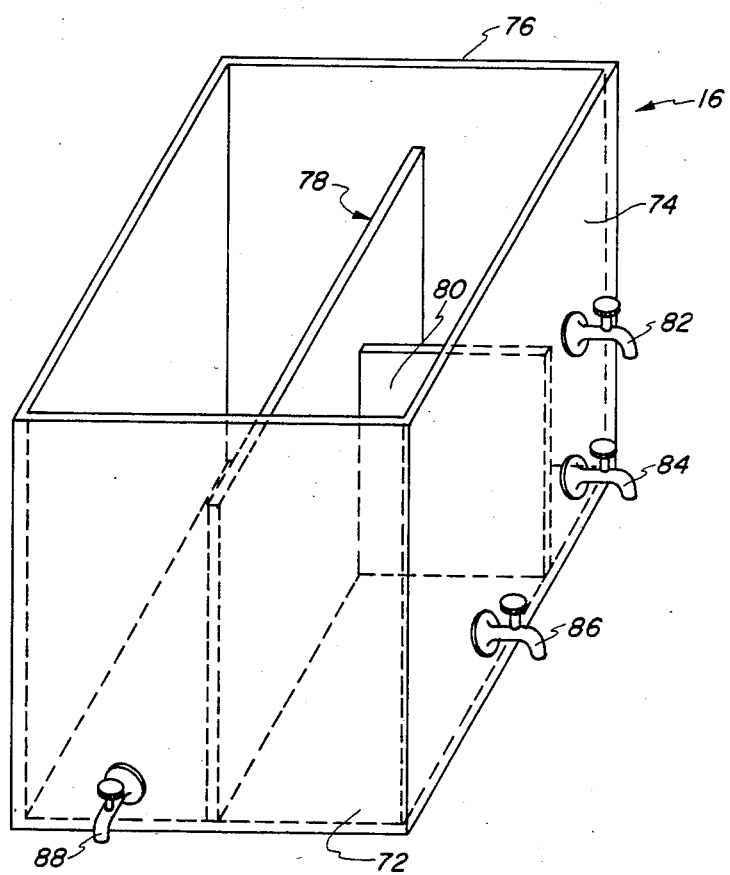
FIG. 4 illustrates is an isometric view partititions or walls in a container with drain valves to control water levels so one division could be damp when other would be dry.

FIG. 4 shows worm container body 16 with separators 78 and 80 at various heights. Valves 82, 84, 86 and 88 may be connected into the various separate compartments to control the water level in each compartment. The separators may be so constructed that they prevent water flowing from one compartment such as 74 to another 72 or may be porous to allow liquid to flow from one compartment to another. The separators are lower than the top rim 76 of the container.

Figure 5:
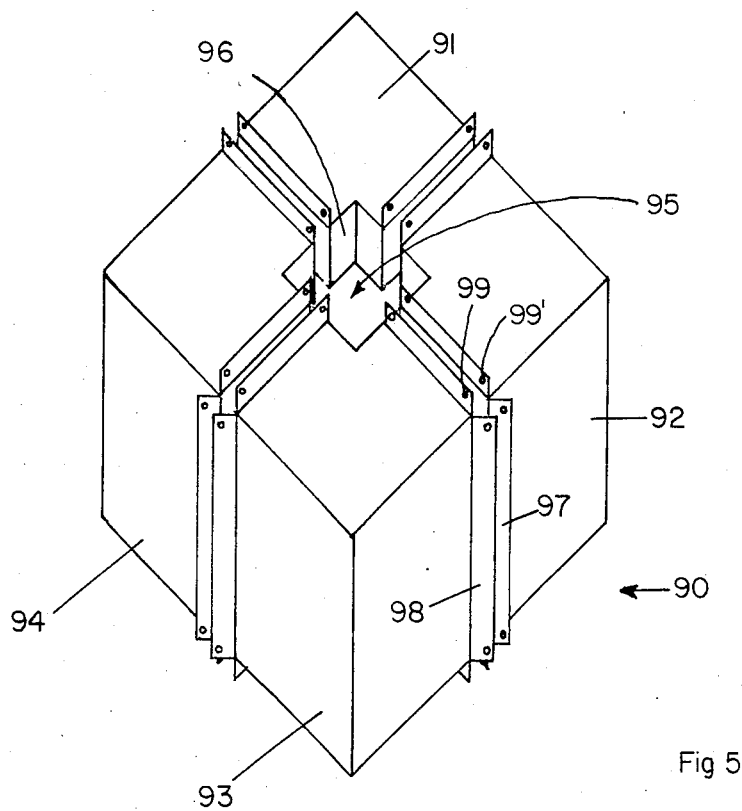
FIG. 5 is an isometric view of a separatable container.

The container may be separatable into parts as shown in FIG. 5. Container 90 has four sections 91, 92, 93 and 94. This container has aperture 95 with aperture sides 96. A channel (not shown) may also be constructed around the aperture 95. The flanges such as 97 and 98 on different sections may be held together by fasteners using mating openings 99 and 99'.

Figure 6:
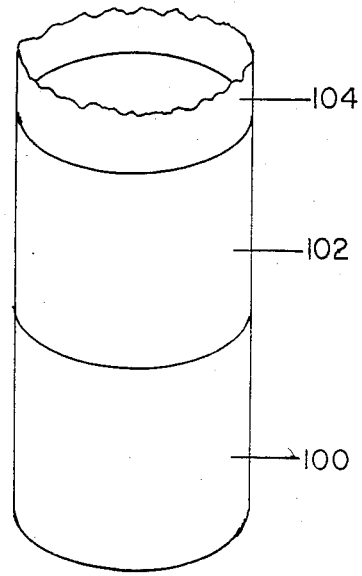
FIG. 6 illustrates a stack of cylindrical containers.

FIG. 6 is illustrated to show that containers 100, 102 and 104 may be stacked to any height with or without bottoms and tops in an intermediate container such as 102.

It should be noted that the channel may be generally wedge shaped to allow upward movement of ice in cold weather climates. This V-shaped design will prevent damage due to freezing.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A worm breeder comprising:
   (a) a container including a bottom wall and a peripheral wall polygonal in cross section, said peripheral wall connected to said bottom wall to define a chamber for confining worms therein, the top of said peripheral wall being so constructed to provide an opening communicating with the ambient and the interior of said chamber;
   (b) wall means disposed within the interior of said chamber and in contact with the interior surface of said container peripheral wall for providing moat chamber within said container chamber, said moat chamber adapted to contain a liquid for preventing ingress of insects into said container chamber,
      said moat wall means including a wall having a height greater than the height of said peripheral container wall; and
   (c) closure means for said container and attached thereto, said closure means including a top wall provided with an opening and a peripheral wall having substantially the same internal dimensions as said container peripheral wall, said closure means including wall means in engagement with the moat wall having the greater height to thereby provide a space therebetween,
      said space communicating with the ambient and the interior of said moat whereby insects crawling up the container wall will be prevented from entering said container chamber.

2. A worm breeder as recited in claim 1 wherein said closure top wall includes means preventing worm from escaping from the interior of said container chamber.

3. A worm breeder as recited in claim 1 wherein said closure means includes a wall disposed substantially parallel to the bottom wall of said container, said wall having a free end in engagement with the free end of said moat wall.

4. A worm breeder as recited in claim 1 wherein said moat means surrounds substantially the entire inner periphery of said container wall.

5. A worm breeder as recited in claim 1 wherein said chamber includes an earthy material for providing a habitat for worms.

6. A worm breeder as recited in claim 1 including a stack of the breeders as defined in claim 1.

* * * * *